US011307130B2

(12) United States Patent
Mainwaring et al.

(10) Patent No.: US 11,307,130 B2
(45) Date of Patent: Apr. 19, 2022

(54) INDICATING SOIL ADDITIVES FOR IMPROVING SOIL WATER INFILTRATION AND/OR MODULATING SOIL WATER REPELLENCE

(71) Applicant: BASF SE, Ludwigshafen (DE)

(72) Inventors: David Edward Mainwaring, Hawthorn (AU); Pandiyan Murugaraj, Hawthorn (AU); Rohan Davies, Melbourne (AU); Klaus Däschner, Limburgerhoff (DE); Alexander Wissemeier, Limburgerhoff (DE); Hao Hao, Hawthorn (AU)

(73) Assignee: BASF SE, Ludwigshafen (DE)

( * ) Notice: Subject to any disclaimer, the term of this patent is extended or adjusted under 35 U.S.C. 154(b) by 171 days.

(21) Appl. No.: 16/758,075

(22) PCT Filed: Nov. 5, 2018

(86) PCT No.: PCT/EP2018/080202
§ 371 (c)(1),
(2) Date: Apr. 22, 2020

(87) PCT Pub. No.: WO2019/086678
PCT Pub. Date: May 9, 2019

(65) Prior Publication Data
US 2020/0363311 A1    Nov. 19, 2020

(30) Foreign Application Priority Data
Nov. 6, 2017    (EP) .................................... 17200207

(51) Int. Cl.
*G01N 15/08*    (2006.01)
*G01N 33/24*    (2006.01)
*C09K 17/14*    (2006.01)

(52) U.S. Cl.
CPC ......... *G01N 15/0826* (2013.01); *G01N 33/24* (2013.01); *G01N 2033/245* (2013.01)

(58) Field of Classification Search
CPC ........ C09K 17/00; C09K 17/14; G01N 15/08; G01N 15/0826; G01N 33/24; G01N 2033/245
See application file for complete search history.

(56) References Cited

U.S. PATENT DOCUMENTS 6,675,529 B1 * 1/2004 Petrea ..................... A01G 24/42
                                                  47/58.1 SC
6,948,276 B2 * 9/2005 Petrea ..................... C09K 17/18
                                                  47/58.1 SC
(Continued)

FOREIGN PATENT DOCUMENTS

CA    2281164 A1 *  2/2001  ............. C09K 17/14
CN    105784564 A *  7/2016  ............... G01N 1/14
(Continued)

OTHER PUBLICATIONS

International Application No. PCT/EP2018/080202, International Search Report and Written Opinion, dated Jan. 18, 2019.
(Continued)

*Primary Examiner* — Nguyen Q. Ha
(74) *Attorney, Agent, or Firm* — Marshall, Gerstein & Borun LLP

(57) ABSTRACT

The present invention is related to a method for indicating soil additives for improving soil water infiltration and/or modulating soil water repellence, a corresponding arrangement and the use thereof.

15 Claims, 12 Drawing Sheets

(56) References Cited

U.S. PATENT DOCUMENTS

| | | |
|---|---|---|
| 9,534,464 B1 | 1/2017 | Kelley et al. |
| 2017/0064900 A1 | 3/2017 | Zemenchik |
| 2020/0140756 A1 * | 5/2020 | Merrill ............... C05C 9/00 |

FOREIGN PATENT DOCUMENTS

| | | | | |
|---|---|---|---|---|
| CN | 107957383 A | * | 4/2018 | ........... G01N 1/286 |
| CN | 109444016 A | * | 3/2019 | ........... C09K 17/14 |
| EP | 1329148 A1 | | 7/2003 | |
| WO | WO-2006125644 A1 | * | 11/2006 | ........... G01N 1/286 |
| WO | WO-2012022164 A1 | * | 2/2012 | ........... C05G 5/30 |
| WO | WO-2013128232 A1 | * | 9/2013 | ........... G01N 1/14 |
| WO | WO-2013/181240 A2 | | 12/2013 | |
| WO | WO-2016/113727 A2 | | 7/2016 | |
| WO | WO-2016/162371 A1 | | 10/2016 | |
| WO | WO-2016/182918 A1 | | 11/2016 | |
| WO | WO-2017/198588 A1 | | 11/2017 | |
| WO | WO-2018/141913 A1 | | 8/2018 | |
| WO | WO-2018/158675 A1 | | 9/2018 | |
| WO | WO-2019/012377 A1 | | 1/2019 | |
| WO | WO-2019/012378 A1 | | 1/2019 | |
| WO | WO-2019/012379 A1 | | 1/2019 | |
| WO | WO-2019/012380 A1 | | 1/2019 | |
| WO | WO-2019/012381 A1 | | 1/2019 | |
| WO | WO-2019/012382 A1 | | 1/2019 | |
| WO | WO-2019/012383 A1 | | 1/2019 | |
| WO | WO-2019/035069 A1 | | 2/2019 | |
| WO | WO-2019/086678 A1 | | 5/2019 | |

OTHER PUBLICATIONS

Johnson et al., A field method for measurement of infiltration, Geological Survey Water-Supply Paper 1544-F, U.S. Geological Survey, 31 pp (Dec. 31, 1963).

Zontek et al., Understanding the different wetting agent chemistries, USGA Green Section Record vol. 50(15), 6 pp. (Jul. 20, 2012).

* cited by examiner

Prior to Infiltration:

During Infiltration:

advancing wetting front during infiltration

A: Water level
B: water-dry soil interface
C: wet soil-dry soil interface

INDICATING SOIL ADDITIVES FOR IMPROVING SOIL WATER INFILTRATION AND/OR MODULATING SOIL WATER REPELLENCE

FIELD OF THE INVENTION

The present invention is related to a method for indicating soil additives for improving soil water infiltration and/or modulating soil water repellence, a corresponding arrangement and the use of the corresponding arrangement.

BACKGROUND OF THE INVENTION

Deficient soil water infiltration is a serious problem affecting many areas of agricultural production. Soil water infiltration describes the process by which water on the ground surface enters the soil. Soil water repellency describes a physical property of soils in terms of hydrophobic or water repelling behavior of the soil preventing the infiltration of water into the soil profile, i.e. the soil does not spontaneously wet when a drop of water is applied to the surface. For efficient agricultural use, the soil is too hydrophobic.

US 20170064900 A1 describes systems and methods for controlling an agricultural system based on soil analysis. The therein described agricultural systems include an agricultural soil analyzer positioned forward of a ground engaging tool relative to a direction of travel of the agricultural system. The therein described agricultural soil analyzer is configured to output a first signal indicative of a parameter of soil forward of the soil conditioner relative to the direction of travel. The therein described agricultural system also includes a controller communicatively coupled to the agricultural soil analyzer.

EP 1329148 A1 describes methods and compositions to reduce soil water repellency. The therein describes methods involve taking a soil sample using a soil probe on a robot platform by moving the robot platform over the soil. The therein described approach further provides that the soil sample is analysed in a lab on the robot platform and the data is generated from the soil analysis. The generated data is transmitted to a remote site using a robotic vehicle.

U.S. Pat. No. 9,534,464 B1 describes soil sampling assemblies. The therein described soil sampler assemblies include a utility vehicle and a soil sampler module coupled to the utility vehicle. The therein described utility vehicle includes a cab, and the soil sampler module is configured to deposit a soil sample in the cab. For example, the therein described soil sampler assemblies include a conveyor system configured to convey the soil sample to the cab. The conveyor system includes a central conveyor and a lateral conveyor that feeds the central conveyor. The central conveyor is on a travel track.

Accordingly, it is an object of the present invention to provide improved soil water infiltration.

SUMMARY OF THE INVENTION

The foregoing and other objects are solved by the subject-matter of the present invention.

According to a first aspect of the present invention, a method for indicating soil additives for improving soil water infiltration and/or modulating soil water repellence is provided, the method comprising the steps of:
providing at least one soil sample;
preparation processing of the at least one soil sample;
providing at least one predefined amount of water to the at least one soil sample;
determining an absorbed amount of water of the at least one soil sample due to contact of the at least one soil sample with the at least one provided and predefined amount of water;
calculating an infiltration rate of the at least one soil sample based on the determined absorbed amount of water and degree of water saturation; and
indicating at least one soil additive to be used out of a list of multiple soil additives based on the calculated infiltration rate of the at least one soil sample.

The present invention provides an indication and recommendation for an appropriate selection of a soil additive e.g. selected from multiple available surfactants decision improving soil water infiltration and/or modulating—for instance reducing—soil water repellence.

According to one embodiment of the present invention, the step of preparation processing comprises:
sieving the at least one soil sample; and/or
air drying the at least one soil sample.

According to another embodiment of the present invention, at least one of the steps of the method is performed by high-throughput screening.

According to one embodiment of the present invention, the step of determining the absorbed amount of water of the at least one soil sample due to contact of the at least one soil sample with the at least one provided and predefined amount of water comprises:
recording of a wetting front over time by optical sample inspection; and/or
using an infiltrometer; and/or
using a permeameter.

According to another embodiment of the present invention, the step of calculating the infiltration rate of the at least one soil sample based on the determined absorbed amount of water comprises:
calculating a water infiltration time; and/or
calculating a water holding capacity.

According to still another embodiment of the present invention, the step of indicating at least one soil additive to be used based on the calculated infiltration rate of the at least one soil sample out of a list of multiple soil additives comprises:
indicating a type of the at least one soil additive to be used; and/or
indicating a concentration of the at least one soil additive to be used; and/or
indicating an amount of the at least one soil additive to be used.

According to a further embodiment of the present invention, the method further comprises the step of providing at least one soil condition and wherein the indicating of the at least one soil additive to be used is further based on the provided, at least one soil condition.

In other words, the soil condition—for instance soil moisture—may be correlated to weather forecast. In addition, soil conditions at a future date or at a future point in time may be correlated to weather forecast relating to the future date or the future point in time.

According to a further embodiment of the present invention, the current diagnostic device and protocol or method determines the benefit of surfactant use in the water infiltration in various soils and the optimal surfactant type for the particular soil, when the soils are dry (dried to a standard degree) characteristic of dry seeding.

According to a further embodiment of the present invention, the device and protocol is configured to build a correlation to provide the relationship between water infiltration and initial soil moisture level.

This allows judgements to be made on:
(a) value of surfactant usage and best surfactant when seeding under more moist soil conditions; and
(b) the impact of surfactant under forecasted seasonal rainfall as announced by weather forecast. That is, surfactant usage can be assessed under predictive weather and soil conditions both at seeding times and future growing seasons. Hence, the present invention provides to not just a purely diagnostic approach, but also a controlling of soil parameters in terms of a prognostic outcome.

In other words, the moisture in soil may be controlled as parameter of function describing the interface conditions and the saturation of the soil water infiltration and/or the soil water repellence.

According to one embodiment of the present invention, the at least one soil additive indicated in the step of indicating the soil surfactant is selected from surfactants, preferably from non-ionic surfactants, in particular from non-ionic surfactants selected from the group consisting of ethylene oxide/propylene oxide block copolymers and $C_6$-$C_{20}$-alkylpolyglycosides.

According to one embodiment of the present invention, the at least one soil additive may for instance comprise a surfactant, a mixture of surfactants, or a mixture of a surfactant and a hydrotropic agent that may be a surfactant.

According to one embodiment of the present invention, the at least one soil additive may for instance comprise a surfactant and/or a surfactant combination.

According to a second aspect of the present invention, an arrangement for indicating soil additives for improving soil water infiltration and/or modulating soil water repellence is provided, the arrangement comprising:
sample providing means configured to provide at least one soil sample;
sample preparation means configured to perform preparation processing of the at least one soil sample;
water providing means configured to provide at least one predefined amount of water to the at least one soil sample;
water amount determining means configured to determine an absorbed amount of water of the at least one soil sample due to contact of the at least one soil sample with the at least one provided and predefined amount of water;
infiltration rate calculating means configured to calculate an infiltration rate of the at least one soil sample based on the determined absorbed amount of water and degree of water saturation;
indicating means configured to indicate at least one soil additive to be used out of a list of multiple soil additives based on the calculated infiltration rate of the at least one soil.

According to a further embodiment of the present invention, the arrangement is a handheld arrangement.

According to a further embodiment of the present invention, the arrangement is configured to perform high-throughput screening.

According to a further embodiment of the present invention, the sample preparation means are configured to
sieve the at least one soil sample; and/or
perform air drying of the at least one soil sample.

According to a third aspect of the present invention, the use of an arrangement according to any implementation form of the second aspect of the present invention is provided for indicating at least one soil additive for improving soil water infiltration and/or modulating—preferably reducing—soil water repellence.

According to a further embodiment of the present invention, the use is for indicating at least one soil additive selected from surfactants, preferably from non-ionic surfactants, in particular from non-ionic surfactants selected from the group consisting of ethylene oxide/propylene oxide copolymers and alkylpolyglycosides.

A computer program performing the method of the present invention may be stored on a computer-readable medium. A computer-readable medium may be a floppy disk, a hard disk, a CD, a DVD, an USB (Universal Serial Bus) storage arrangement, a RAM (Random Access Memory), a ROM (Read Only Memory) and an EPROM (Erasable Programmable Read Only Memory).

A computer-readable medium may also be a data communication network, for example the Internet, which allows downloading a program code.

The methods, systems and arrangements described herein may be implemented as software in a Digital Signal Processor, DSP, in a micro-controller or in any other sideprocessor or as hardware circuit within an application specific integrated circuit, ASIC, CPLD or FPGA.

The present invention can be implemented in digital electronic circuitry, or in computer hardware, firmware, software, or in combinations thereof, e.g. in available hardware of conventional mobile arrangements or in new hardware dedicated for processing the methods described herein.

BRIEF DESCRIPTION OF THE DRAWINGS

A more complete appreciation of the invention and the attendant advantages thereof will be more clearly understood by reference to the following schematic drawings, which are not to scale, wherein.

DETAILED DESCRIPTION OF EMBODIMENTS

Figure 1:
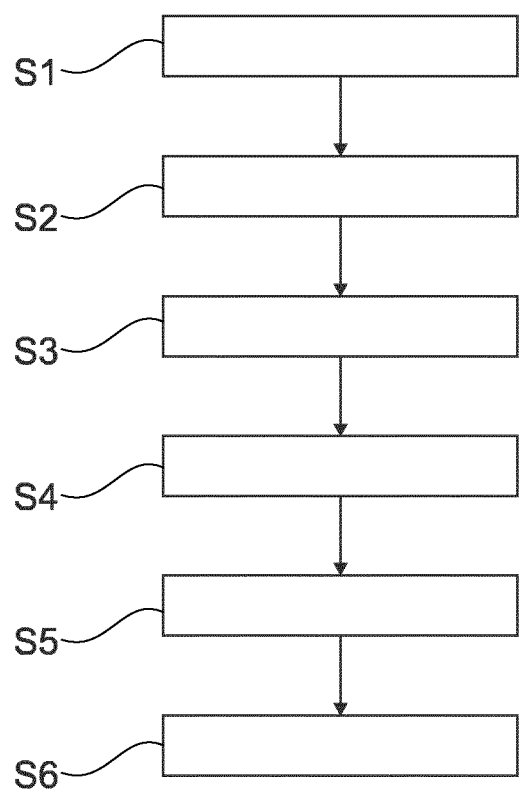
FIG. 1 shows a schematic flowchart diagram of a method for indicating soil additives for improving soil water infiltration and/or modulating soil water repellence according to an exemplary embodiment of the invention.

The illustration in the drawings is schematically and not to scale. In different drawings, similar or identical elements are provided with the same reference numerals. Generally, identical parts, units, entities or steps are provided with the same reference symbols in the figures.

The improving of soil water infiltration may comprise decreasing or increasing the water absorption capacity of the soil. Further, it may also comprise decreasing or increasing the amount of absorbed water which is currently present in the soil or which will be according to a forecast present in the soil.

In other words, the present invention advantageously provides controlling movement or flow of water in the soil, for instance from the soil surface into the soil, or for instance from ground water to higher layers of soil. Thus, the present invention advantageously provides to modulate and adjust the infiltration and/or redistribution of water in soil.

For instance, in the event that high—for instance 100 mm rain quantities are announced by a weather report for the upcoming 3 or 4 days, a decreasing of the water absorption capacity of the soil may be required in case that plants with basic dry soil conditions are located on a field. In particular, the decreased water absorption capacity of the soil will help to provide a quicker drying of the soil after the precipitation.

According to an exemplary embodiment, the present invention may advantageously be used to control the distribution of water into certain depths of the soil profile.

FIG. 1 shows a schematic flowchart diagram of a method for indicating soil additives for improving soil water infiltration and/or modulating—preferably reducing—soil water repellence according to an exemplary embodiment of the invention.

The method for indicating soil additives for improving soil water infiltration and/or modulating soil water repellence may comprise at least the following steps:

As a first step of the method, providing S1 at least one soil sample may be conducted.

The providing of the least one soil sample may for instance be achieved in terms of cutting out a soil sample from the soil. The cut out in terms of the least one soil sample may be of circular or rectangular or elliptical shape.

As a second step of the method, preparation processing S2 of the at least one soil sample may be performed.

The preparation processing S2 may comprise sieving the at least one soil sample. The sieving may be performed by mechanical sieving.

According to an exemplary embodiment, the step of preparation processing S2 comprises: sieving the at least one soil sample; and/or air drying the at least one soil sample. The sieving may for instance be performed in order to remove pebbles and rocks, further the sieving may be conducted in order to break up soil aggregates.

According to an exemplary embodiment, the sieving may use different sieves with various meshes. For example, mesh sizes between 0.1 mm and 2 mm, preferably between 0.1 mm and 1.5 mm, more preferably between 0.2 mm and 1 mm and most preferably between 0.3 mm and 0.75 mm may be used.

According to an exemplary embodiment, the sieving may use different sieves with various meshes sizes ranging from 0.1 mm to 2 mm. A larger size column may accommodate sizes up to 5 mm.

Optionally, natural non-sieved soil may be examined.

According to an exemplary embodiment, perforated plates sieves or wire sieves may be used. The sieving may be performed by an automated sieving apparatus.

According to an exemplary embodiment, the step of preparation processing S2 comprises: sieving to a maximum particle size of up to 5 mm, or preferably of up to 2 mm, or most preferably of up to 1 mm with a woven sieve.

According to an exemplary embodiment, the step of preparation processing S2 comprises: column packing of the at least one soil sample.

Further, the preparation processing S2 may comprise air drying the at least one soil sample.

According to an exemplary embodiment, the step of air drying the at least one soil sample may be performed at a temperature of up to 50° C., or preferably of up to 45° C., or more preferably of up to 40° C., or most preferably of up to 35° C. in a vented or non-vented oven for up to 12 hours, or preferably up to 24 hours, or more preferably up to 36 hours, or most preferably up to 72 hours.

As a third step of the method, providing S3 at least one predefined amount of water to the at least one soil sample may be conducted.

According to one embodiment of the present invention, the providing S3 of the at least one predefined amount of water may be performed by providing a single amount of water For instance 1 ml or 2 ml or 10 ml or 50 ml of water may be provided with regard to a certain sample size of the at least one soil sample.

According to one embodiment of the present invention, the providing S3 of the at least one predefined amount of water may be performed by periodical providing multiple quantities of water.

According to one embodiment of the present invention, the providing S3 of the at least one predefined amount of water may be performed by continuously providing a constant or non-constant flow of water, for instance a flow of 1 ml per minute or 2 ml per minute or 10 ml per minute or 50 ml of water per minute.

As a fourth step of the method, determining S4 an absorbed amount of water of the at least one soil sample due to contact of the at least one soil sample with the at least one provided and predefined amount of water may be performed.

According to one embodiment of the present invention, the step of determining S4 the absorbed amount of water of the at least one soil sample due to contact of the at least one soil sample with the at least one provided and predefined amount of water comprises:

recording of a wetting front over time by optical sample inspection; and/or
using an infiltrometer; and/or
using a permeameter.

The term "infiltrometer" as used by the present invention refers to an arrangement used to measure a rate of water infiltration into soil or other porous media. An infiltrometer may for instance be a single ring infiltrometer.

The term "permeameter" as used by the present invention refers to an arrangement used for measuring water infiltration in the soil, which is characterized by in situ saturated and unsaturated soil hydraulic properties. It is mainly used to provide estimates of the hydraulic conductivity of the soil near saturation.

The terms "permeameter" and "hydraulic conductivity" as used by the present invention refer to hydraulic transport in soil under saturation conditions, hence the issue is the possible effect of surfactant addition on transport when the soil is saturated. In such a soil, there is no air—water interface hence there is no capillary suction to be enhanced by surfactants lowering the interfacial tension at the meniscus.

The term "soil additive" as used by the present invention may refer to any surface active substance altering the soil water infiltration or soil water repellency, including—but not limited to—non-ionic surfactants, in particular non-ionic surfactants selected from the group consisting of ethylene oxide/propylene oxide, block copolymers and C6-C20-alkylpolyglycosides or even proteins or other natural substances. The term "soil additive" as used by the present invention may refer to an additive altering the surface tension or interfacial tension between a liquid and a solid, e.g. between a ground-penetrating liquid and the ground.

The term "surface active substance" as used by the present invention may refer to a substance altering the surface tension between a ground-penetrating liquid and the ground for instance in terms of the following values:

Surface tension of preferably 25 to 55 mN/m, more preferably of 30 to 50 mN/m, more preferably of 33 to 47 mN/m, and particularly of 36 to 43 mN/m, at a concentration of 1 g/L in water at 23° C. as measured according to DIN 53914.

For instance, the interaction of the ground-penetrating liquid and the ground by using the surface active substance may be defined by a wetting power of preferably >50 sec, more preferably >100 sec, most preferably >150 sec, particularly preferably >200 sec, particularly >250 sec as measured according to EN 1772 (1 g/L distilled water with 2 g/L soda ash at 23° C.).

For instance the surface active substance may have a foam formation of preferably <100 ml, more preferably <50 ml, most preferably <20 ml, particularly <10 ml as measured according to EN 12728, 40° C., 2 g/l in water with 1.8 mmol Ca2+-Ions/l, after 30 sec).

The term "improving soil water infiltration" as well as "modulating soil water repellence" as used by the present invention may be understood as follows:

The abbreviation wt.-% stands for "percent by weight".

Improving soil water infiltration means that the soil water infiltration measured in case the at least one soil additive has not been applied is lower—preferably 4% lower, most preferably 7% lower, particularly 10% lower, particularly preferably 15% lower, particularly most preferably 20% lower, for example 25% lower—than the soil water infiltration measured in case the soil additive has been applied.

Modulating soil water repellence means that the soil water repellence measured in case the at least one soil additive has not been applied is altered, for instance is higher or lower—preferably 4% higher or lower, most preferably 7% higher or lower, particularly 10% higher or lower, particularly preferably 15% higher or lower, particularly most preferably 20% higher or lower, for example 25% higher or lower—than the soil water repellence measured in case the at least one soil additive has been applied.

The term "at least one soil additive to be used" as used by the present invention provides that at least one soil additive is used as soil additive, e.g. is to be treated on the ground, which includes but is not limited to applying, especially applying to the surface of the area of the soil, groundcover, spraying, dripping together with irrigation, applying as in-furrow irrigation, applying during or together with irrigation or fertigation. "Treating" includes but is not limited to mixing into the soil, mixing to the potting mix e.g. during its production.

The term "groundcover" as used by the present invention includes, but is not limited to, soil, natural soil, potting soil, sand, silt, clay, turfgrasses and other plants and forms of vegetation used to cover and protect the soil, as well as composites of organic materials that form within or as part of such groundcovers, such as thatch and mat layers, and also includes potting mixes.

Preferably, groundcover is soil, more preferably, groundcover is water-repellent soil. In another preferred embodiment, groundcover is potting mix. Potting mix, which is also referred to potting soil, is a soilless blend of ingredients that is used to grow plants, preferably, the potting mix comprises a combination of peat moss, vermiculite, coir fiber, perlite, pine bark, sand, compost, and further ingredients.

The present invention may also provide that depending on the strength of adsorption of the surfactant on the soil particles, some surfactant may remain soluble or may be re-solubilized with water ingress. This provides a reduction of the interfacial tension at the advancing wetting front lower in the bed and reducing this constraint would enhance the infiltration rate.

The present invention also allows controlling the interfacial tension of the advancing wetting front.

As a fifth step of the method, calculating S5 an infiltration rate of the at least one soil sample based on the determined absorbed amount of water may be conducted.

As a sixth step of the method, indicating S6 at least one soil additive to be used out of a list of multiple soil additives based on the calculated infiltration rate of the at least one soil sample may be performed.

According to an exemplary embodiment, the step of indicating S6 the at least one soil additive to be used may be perform using a display based on man-machine-interface or graphical interface unit.

According to an exemplary embodiment, the display used to display and to indicate S6 the at least one soil additive to be used may installed on a handheld device or may be a tractor-mounted display unit located in the cockpit of the tractor.

Figure 2:
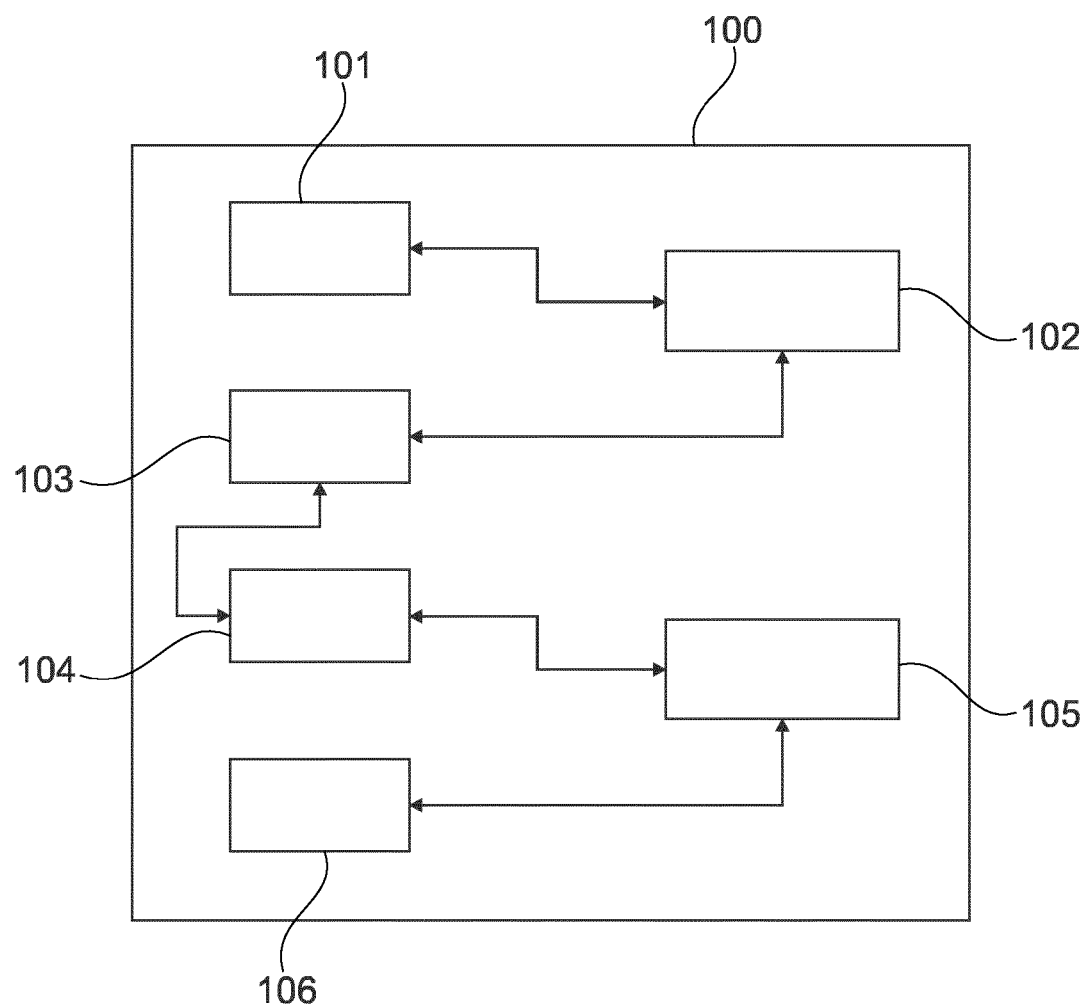
FIG. 2 shows a schematic diagram of an arrangement for indicating soil additives for improving soil water infiltration and/or modulating soil water repellence according to an exemplary embodiment of the invention.

FIG. 2 shows a schematic diagram of an arrangement for indicating soil additives for improving soil water infiltration and/or modulating soil water repellence according to an exemplary embodiment of the invention.

FIG. 2 shows an arrangement 100 for indicating soil additives for improving soil water infiltration and/or modulating soil water repellence.

The arrangement 100 may be integrated in one or in multiple device, e.g. in terms of a distributed computer environment comprising handheld field-deployable unit as well as lab-based analyzing units. These units may be coupled by data transmission connections.

The arrangement 100 comprises sample providing means 101, sample preparation means 102, water providing means 103, water amount determining means 104, as well as infiltration rate calculating means 105, and indicating means 106.

The sample providing means 101 are configured to provide at least one soil sample.

The sample preparation means 102 are configured to perform preparation processing of the at least one soil sample.

The water providing means 103 are configured to provide at least one predefined amount of water to the at least one soil sample.

The water amount determining means 104 are configured to determine an absorbed amount of water of the at least one soil sample due to contact of the at least one soil sample with the at least one provided and predefined amount of water.

The infiltration rate calculating means 105 are configured to calculate an infiltration rate of the at least one soil sample based on the determined absorbed amount of water.

The indicating means 106 are configured to indicate at least one soil additive to be used out of a list of multiple soil additives based on the calculated infiltration rate of the at least one soil sample.

The indicating of the at least one soil additive to be used out of the list of multiple soil additives based on the calculated infiltration rate may for instance performed on a relative evaluation of the determined absorbed amount of water and/or the calculated infiltration rate if for instance compared with other soil samples.

Figure 3:
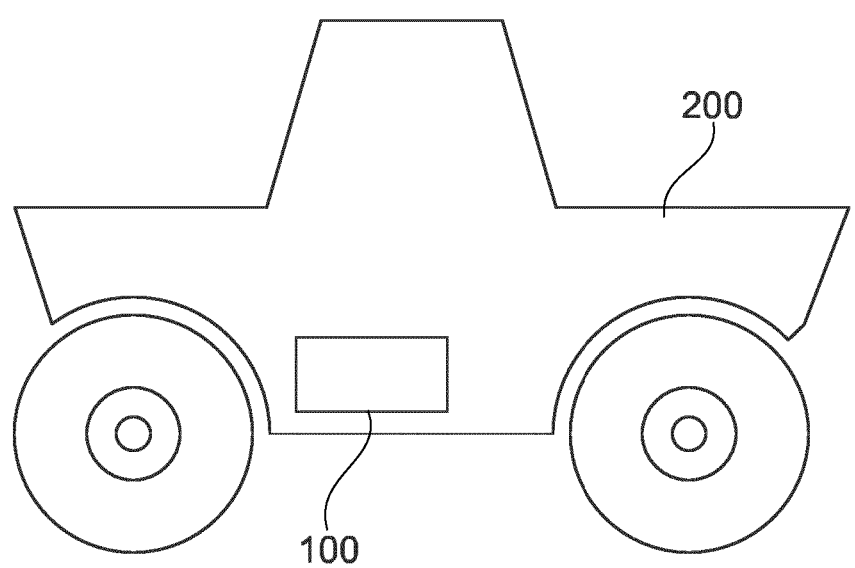
FIG. 3 shows a schematic diagram of a tractor-mounted arrangement for indicating soil additives for improving soil water infiltration and/or modulating soil water repellence according to an exemplary embodiment of the invention.

FIG. 3 shows a schematic diagram of a tractor-mounted arrangement for indicating soil additives for improving soil water infiltration and/or modulating soil water repellence according to an exemplary embodiment of the invention.

According to an exemplary embodiment, the arrangement may be mounted on the chassis of the tractor 200 and may be configured to provide soil samples by using a robotic arm which is also coupled to the tractor 200.

According to an exemplary embodiment the arrangement may mounted on the tractor and may be configured to receive a soil sample from a user, who is manually detaching the soil sample from the soil.

Figure 4:
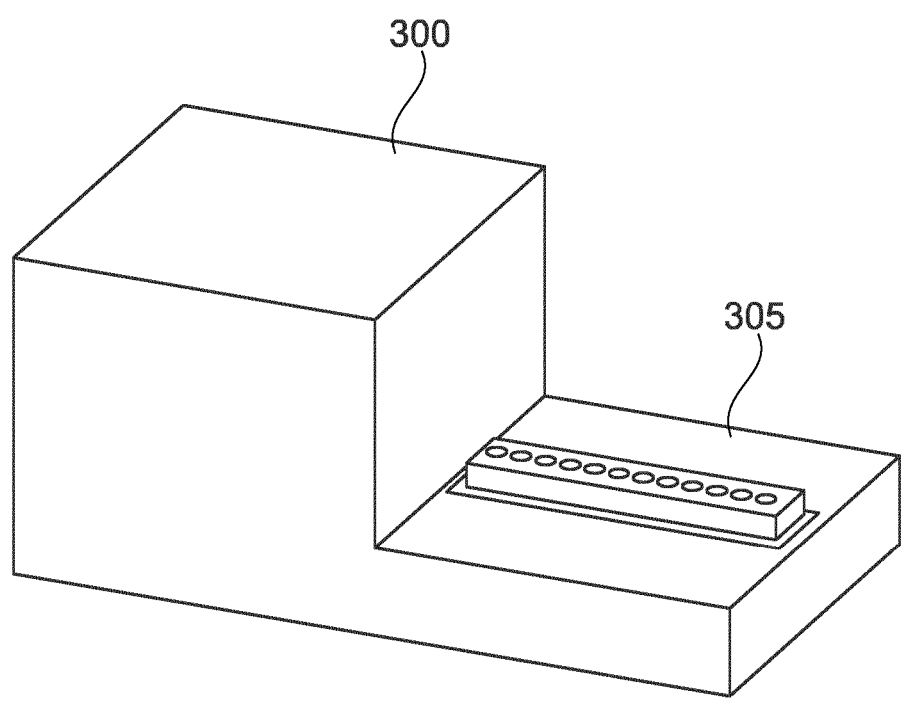
FIG. 4 shows a schematic diagram of a laboratory-based arrangement for indicating soil additives for improving soil water infiltration and/or modulating soil water repellence according to an exemplary embodiment of the invention.

FIG. 4 shows a schematic diagram of a laboratory-based part of the arrangement for indicating soil additives for improving soil water infiltration and/or modulating soil water repellence according to an exemplary embodiment of the invention.

The laboratory-based part of the arrangement may for instance comprise the sample preparation means 102, the water providing means 103 and the water amount determining means 104.

The water amount determining means 104 may be configured to analyze 2-dimensional plates, e.g. a row of soil samples.

The soil samples may for instance be soil sampling cylinders, with a diameter size of 0.5 cm to 10 cm, preferably with a diameter size of 1.0 cm to 5 cm, more preferably with a diameter size of 1.5 cm to 3.5 cm.

The diameter size of the soil samples may for instance be adjusted to a characteristic particle size of the soil, for instance of a typical structure size of the soil microstructure or the size of certain aggregates of the soil.

The diameter size of the soil samples may for instance be 10-times of a typical particle size of 2 mm, e.g. 2 cm.

The height of the soil sampling cylinders may have a size of 5 cm to 20 cm, preferably a size of 7.5 cm to 15 cm, more preferably a size of 8.0 cm to 11.5 cm.

The arrangement for indicating soil additives may be integrated and sizewise adjusted—for instance miniaturized or enlarged.

According to an exemplary embodiment, the arrangement may be a handheld arrangement or a portable arrangement for conducting the method for indicating soil additives for improving soil water infiltration and/or modulating soil water repellence as for instance shown in FIG. 1.

According to an exemplary embodiment, the arrangement may be a laboratory based high throughput screening arrangement 300, by using robotics, data processing and controlling software, liquid handling arrangements, and sensitive cameras, the soil water infiltration tests are automatically conducted using a rack 305 comprising multiple columns, each of which to be filled with at least one soil sample.

Figure 5:
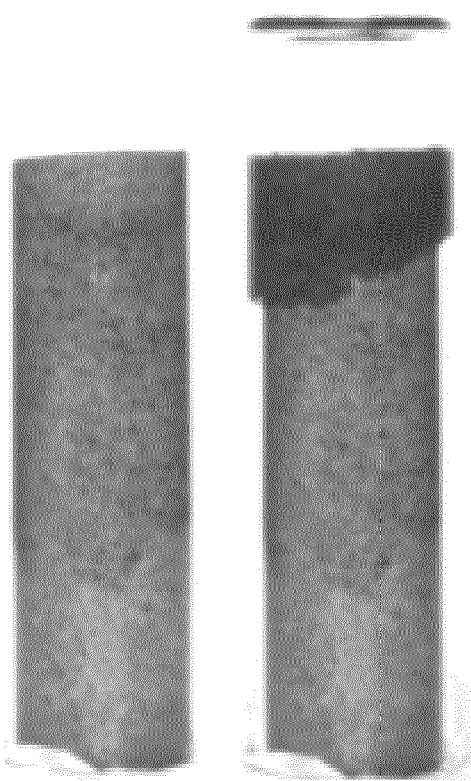
FIG. 5 shows an image of a column before and during infiltration according to an exemplary embodiment of the invention.

FIG. 5 shows an image of a column before and during infiltration according to an exemplary embodiment of the invention.

The images as shown in FIG. 5 depict the moving of the wetting front due to contact of the at least one soil sample with the predefined amount of water. The water front may be determining using image analysis methods, for instance, imaging-based automatic inspection and analysis.

According to an exemplary embodiment, the arrangement may be a handheld arrangement or a portable arrangement.

The scope and interest of the invention will be better understood based on the following examples which are intended to illustrate certain embodiments of the invention and which are non-limitative.

According to a further exemplary embodiment of the present invention, a computer program element may be provided for executing the method for indicating soil additives for improving soil water infiltration and/or modulating soil water repellence.

According to a further exemplary embodiment of the present invention, the computer program element might therefore be stored on a computer unit, which might also be part of an embodiment of the present invention. This computing unit may be adapted to perform or induce a performing of the steps of the method described above.

Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

Figure 6:
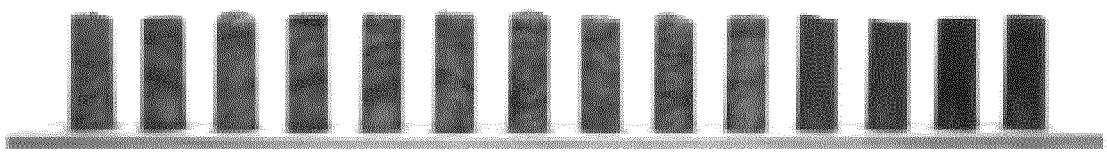
FIG. 6 shows example images taken from a diagnostic test conducted on 14 soils simultaneously according to a further exemplary embodiment of the invention.
Figure 6:
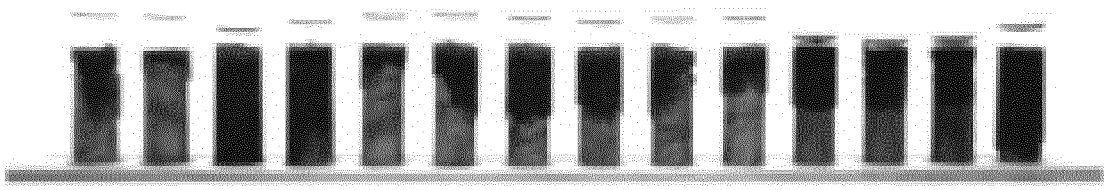

FIG. 6 shows example images taken from a diagnostic test conducted on 14 soils simultaneously according to a further exemplary embodiment of the invention.

Figure 7:
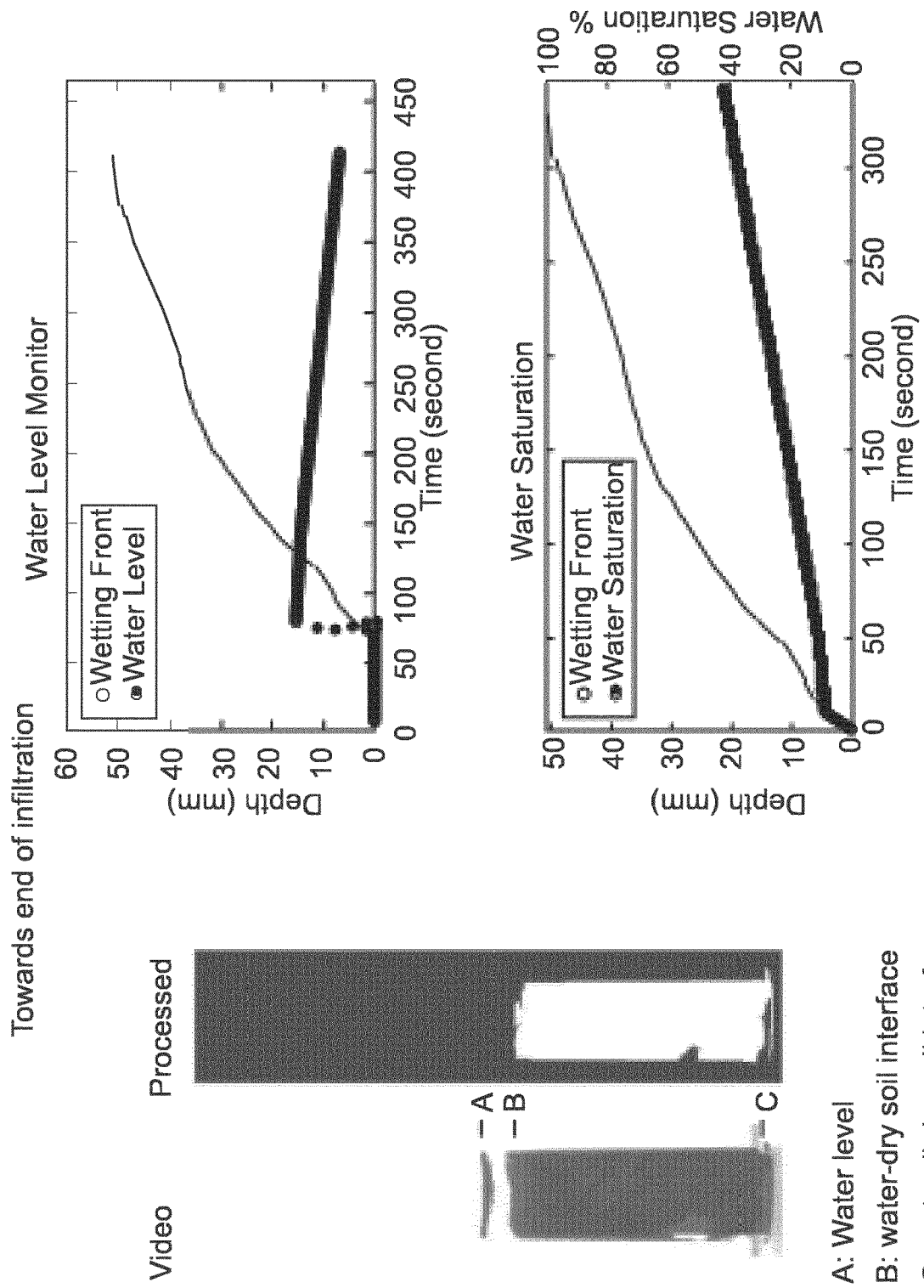
FIG. 7 shows video image during recording plus the computed corresponding image from computer visualization together with the simultaneous graphical data according to a further exemplary embodiment of the invention.

FIG. 7 shows video image during recording plus the computed corresponding image from computer visualization together with the simultaneous graphical data according to a further exemplary embodiment of the invention.

FIG. 7 shows example images: Video image during recording plus the computed corresponding image from computer visualization together with the simultaneous graphical data of (a) Rate of water infiltration (indicative of surfactant reductions in run-off water losses), (b) Pore filling (indicative of water holding capacity during an initial rain event and the extent of preferential flow i.e. water loss through fingering).

According to a further exemplary embodiment of the present invention, the soils were placed in a Tube Rack #2 and inserted in the optical infiltrometer. Samples represent 14 Australian wheat growing soils spanning a wide range of wettabilities (MED values) and with and without the presence of surfactant. The upper image shows the soil samples prior to infiltration, while the lower image depicts the soil samples during infiltration.

According to a further exemplary embodiment of the present invention, real-time screen images of video image are shown during recording plus the computed corresponding image from computer visualization together with the simultaneous graphical data of (a) Rate of water infiltration (indicative of surfactant reductions in run-off water losses), (b) Pore filling (indicative of water holding capacity during an initial rain event and the extent of preferential flow i.e. water loss through fingering).

Figure 8:
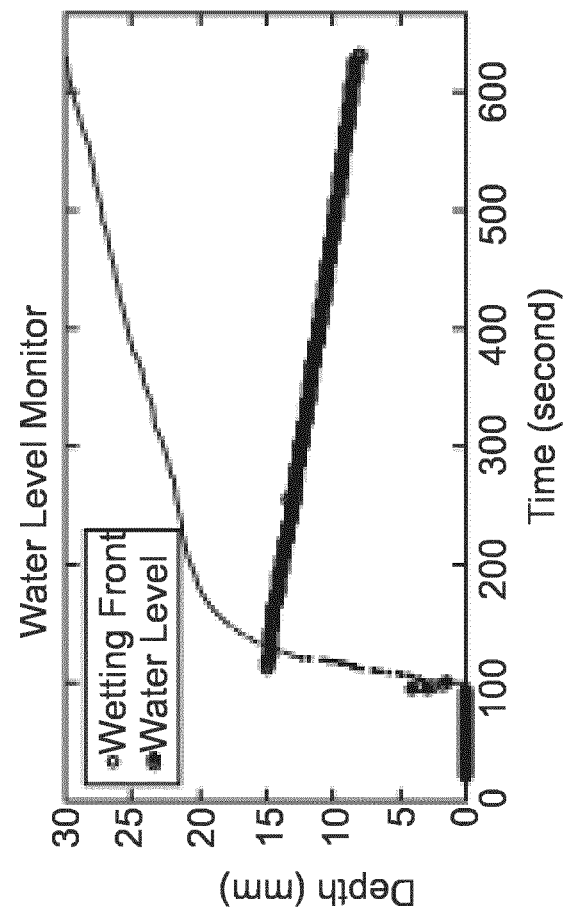
FIG. 8 shows video image during recording plus the computed corresponding image from computer visualization together with the simultaneous graphical data according to a further exemplary embodiment of the invention.
Figure 8:
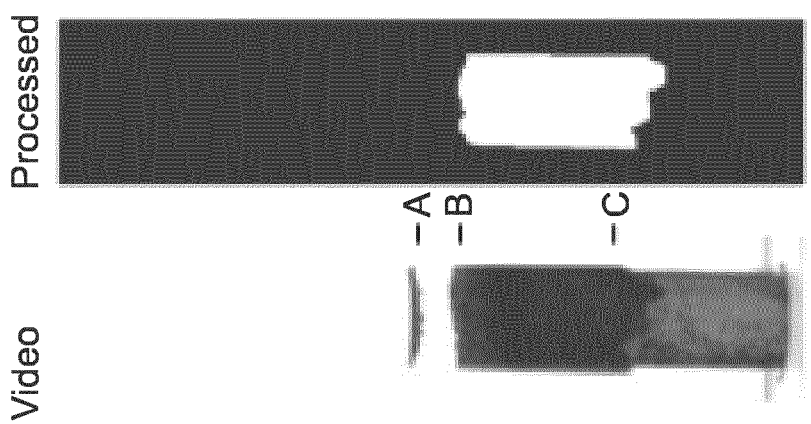

FIG. 8 shows a video image during recording plus the computed corresponding image from computer visualization together with the simultaneous graphical data according to a further exemplary embodiment of the invention.

Figure 9:
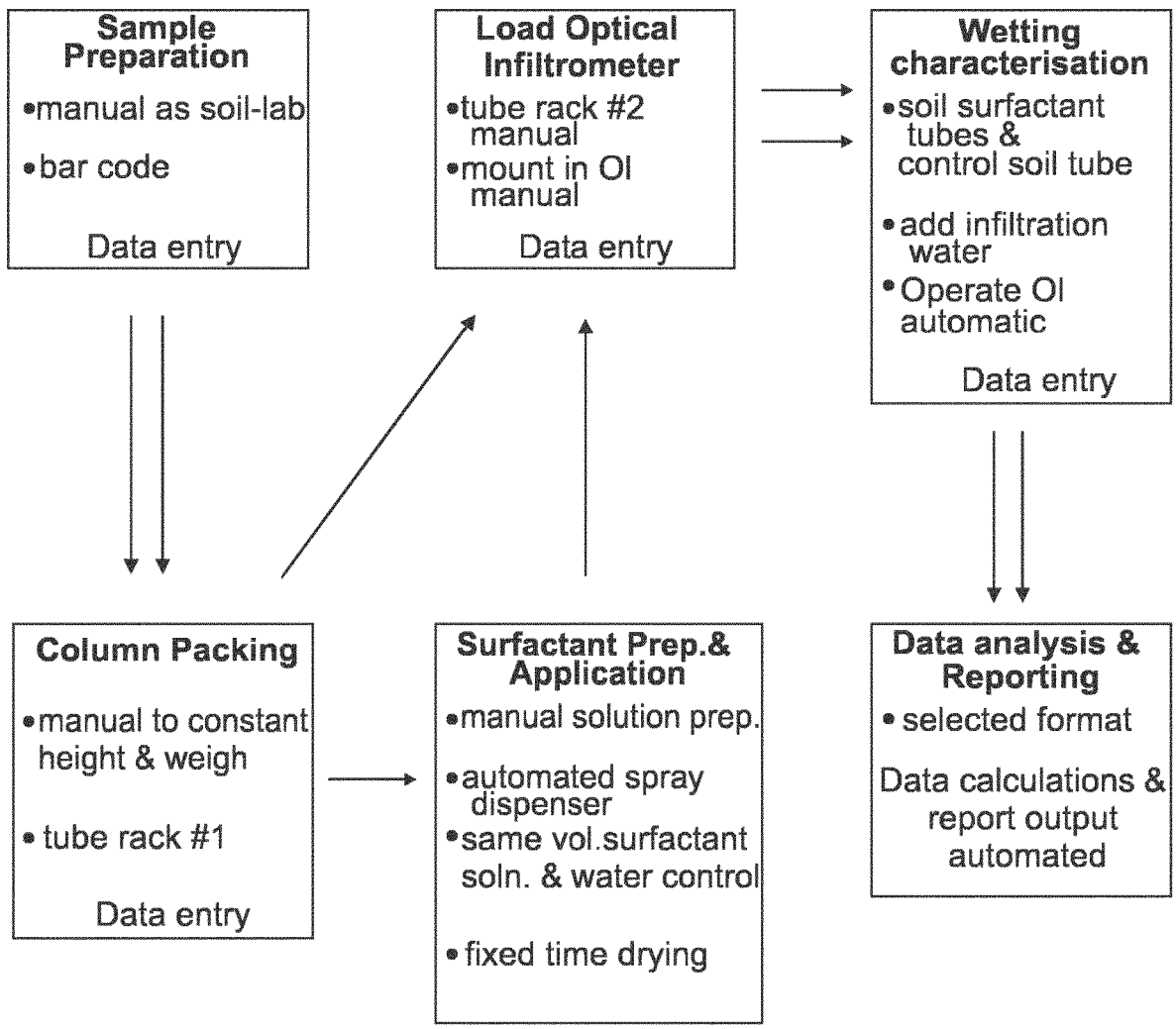
FIG. 9 shows a schematic diagram of a layout of a diagnostic test process according to a further exemplary embodiment of the invention.

FIG. 9 shows a schematic diagram of a layout of a diagnostic test process according to a further exemplary embodiment of the invention. The infiltration testing scheme is for instance devised to conform as closely as possible to the processes and equipment types operated in a conventional commercial "soil testing" laboratory. The soil material flow path and the data input scheme is indicated in grey.

Figure 10:
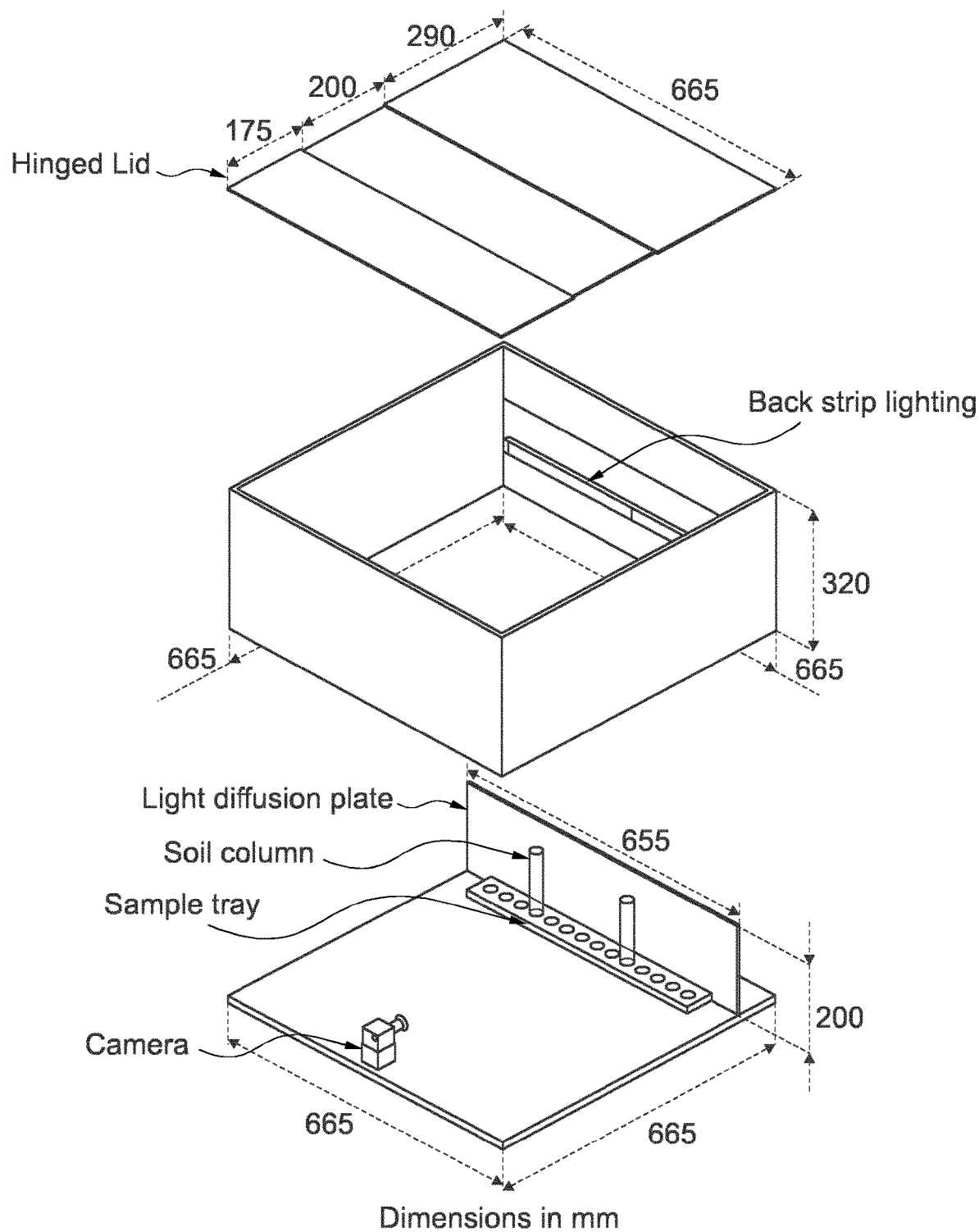
FIG. 10 shows a schematic diagram of device components according to a further exemplary embodiment of the invention.

FIG. 10 shows a schematic diagram of device components according to a further exemplary embodiment of the invention.

Figure 11:
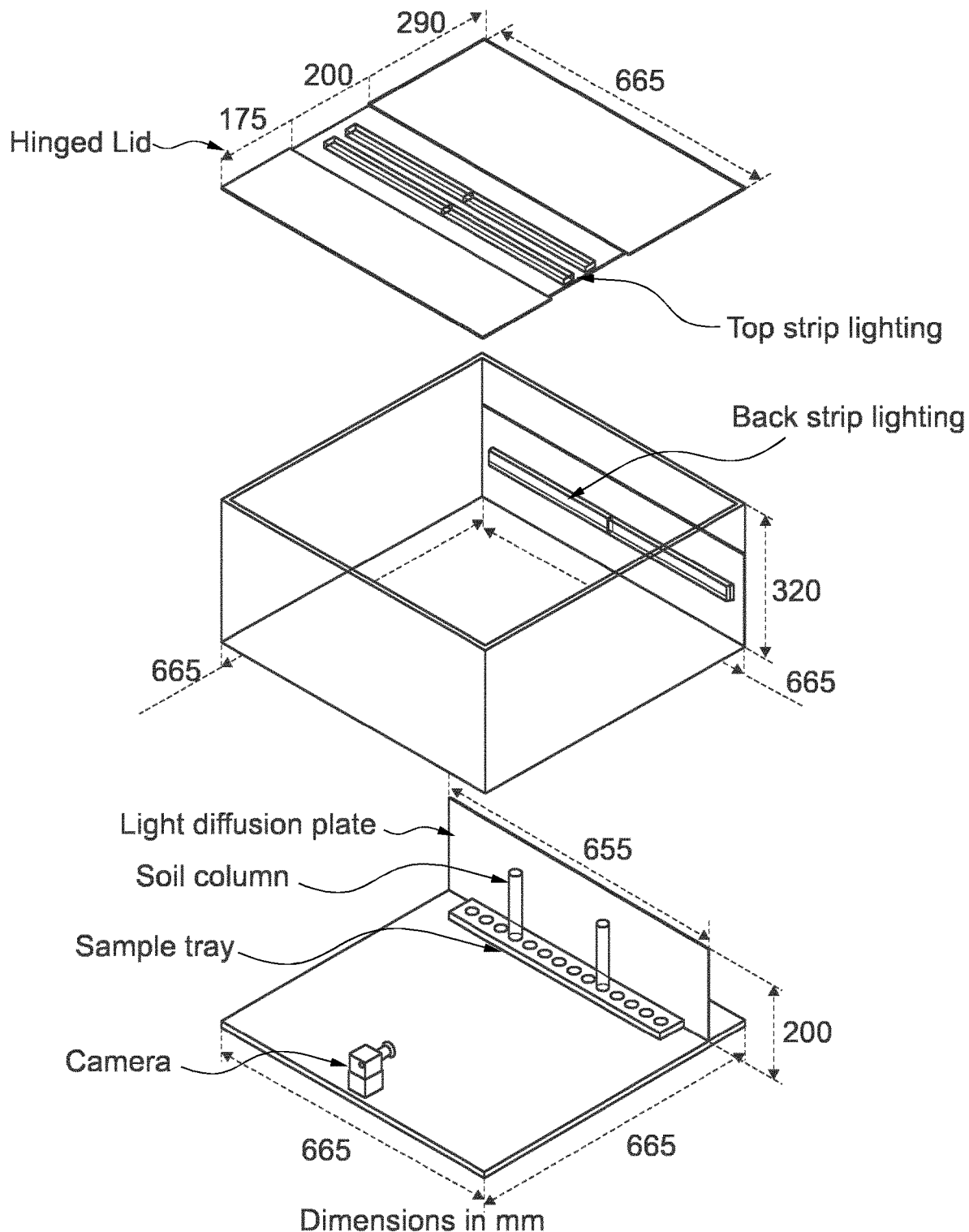
FIG. 11 shows a schematic diagram of device components according to a further exemplary embodiment of the invention.

FIG. 11 shows a schematic diagram of device components according to a further exemplary embodiment of the invention.

Figure 12:
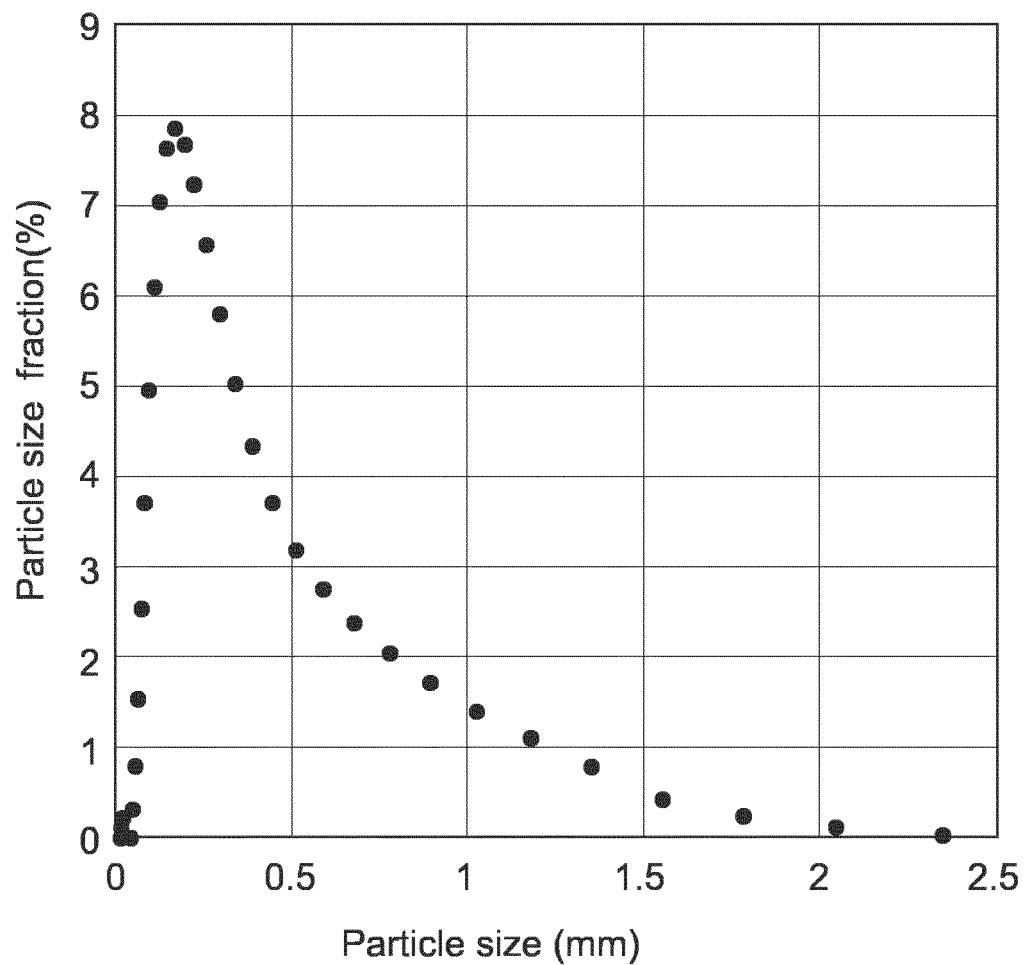
FIG. 12 shows a schematic diagram soil particle size distribution data according to a further exemplary embodiment of the invention.

FIG. 12 shows a schematic diagram soil particle size distribution data according to a further exemplary embodiment of the invention.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network.

According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the arrangement type claims.

However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

EXAMPLES

Method

Example 1

Soil Sample and Preparation:
1. Dry soil 40° C. vented oven for 2 days;
2. No grinding or milling;
3. Sieve to −2 mm with woven sieve removes any visible plant, or visible matter particles.

Column Packing:
1. Column details: 20 mm diameter, height 110 mm, hydrophobic inner surface, porous filter at bottom 11 micron hydrophilic nylon membrane;
2. Weigh column with membrane;
3. Packed with 3 successive soil aliquots with each tapped 3 times between additions. Final height between 7 and 8 cm; (determined automatically by image system)
4. Weigh; (for instance to determine weight of soil per column)
5. As minimum, 3 soil columns packed sequentially with consistent packing procedure Wetting Characteristic of Soil Sample:
1. One of packed columns above, added water to 20 mm on top of soil bed;
2. Simultaneously start recording infiltration image, recording wetting front in soil and decrease in free water level (middle of meniscus);
3. Calculate infiltration rate plus the degree of water retention in bed.

Surfactant Application Protocol:
1. Prepare solutions of surfactants to be tested. Concentration 4 g/L to be applied at 150 µL per soil sample;
2. Application of surfactant by multiple droplets evenly spaced on soil surface;
3. Dried as above 40° C. to constant weight, e.g. till a constant weight is reached;
4. Water infiltration on surfactant amended soil, as above give same data output (time needed ~10-15 min);

5. Calculate amended water infiltration rate and water retention in bed.

Calculation and Reporting:
1. Data input into program to report surfactant amended water infiltration rate (for instance measured in cm/s in soil bed) and surfactant amended water retention as a function of distance in soil bed (for instance measured in % of soil volume filled with water);
2. Reconfigure data output to industry specifications and store primary data for soil type and location.

Utilization of Above Procedure

This procedure may for instance be used as a laboratory practice, which may be translated into the procedure utilizing a multi-sample visualisation/recording system This example may be translated into the customary processes in a soil-testing laboratory

EXAMPLES

Device

Example 2—Titled "Usage of Automated Multi-Sample Infiltration Analysis, and Take Out"

No. of Racks: 10
Automated Multi-Sample Infiltration Analysis
Sample: dried sieved soil
Sample number: 3000
Target time: 8 weeks
Instrument Analysis
Analysis per soil: 1 control+2 treatments
No. individual tubes: 9000
No. Racks: 10
Time per rack: 0.5 hr
Total time: 450 hr
Operating time: 15 hr/day, 5 day/week, 150 racks/week
Time period required: 6 weeks (1 instrument)
Two instruments: ~1 month
Samples/Solutions
Water application to tubes in instrument (fixed amount at test start)
Surfactant solution application to tube (prior to instrument)
Manual packing: 1.5 hr/rack (~3× instrumentation time/rack)

Example 3

Sample Data Sheet for Optical Measurements
1)
Barcode
2)

| | |
|---|---|
| Tube rack identification code | 01 |
| Column identification code | 01-01 |
| Soil Column height | 7.9 cm |
| Soil Column weight | 35.25 g |
| Infiltration measurements | |

3)
Tube rack #2 identification code A
Column identity code A-01
4)
Data
Tube rack #2 identification code A
Column identification code A-01

Wetting depth {cm} vs time {s} {numerical data}
Ponding depth decrease {cm} vs time {numerical data}
5)
Data Analysis
Sample Barcode
Plot of Wetting depth {cm} vs time {s} {numerical data}
Plot Water retention {%} vs time {s} {numerical data}
Report on Soil Hydrophobicity
Report on Soil Hydrophobicity

Example 4

Titled "Soil Sample Handling and Surfactant Analysis Procedure"

Based on Employing the Experimental Swinburne Optical Infiltrometer

A) Soil Sample and Preparation:
1. Dry soil 40 deg. vented oven for 2 days
2. No grinding or milling
3. Sieve to up to 2 mm with woven sieve removes any visible plant, matter, etc.

B) Column Packing:
1. Column details approximately 20 mm diameter, Height 110 mm, hydrophobic inner surface, Porous filter at bottom 11 micron hydrophilic nylon membrane
2. Weigh column with membrane
3. Packed with 3 successive soil aliquots with each tapped 3 times between additions. Final height between 7 and 8 cm. (determined automatically by image system)
4. Weigh (to determine weight of soil per column)
5. As minimum, 3 soil columns packed sequentially with consistent packing procedure C) Surfactant Preparation and Application to Soil:
1. Prepare solutions of surfactants to be tested. Concentration 4 g/L to be applied at 150 μL per soil sample
2. Soil samples (control—soil only, duplicate surfactant amended soil) 3 tubes
3. Application of surfactant by fine spray over soil surface only to duplicate tubes
4. Application of same volume of water to control
5. Dried as above 40° C. for fixed time D) Preparation of Sample Tubes in Optical Infiltrometer:
1. Mount filled sample tubes in tube-rack (control—soil only, duplicate surfactant amended soil)
2. Operate Infiltrometer as per operating manual E) Wetting Characteristic of Soil and Surfactant Modified Soil Samples:
1. Add water to control and surfactant amended columns to 20 mm above top of soil bed (constant volume liquid dispenser)
2. Simultaneously start recording infiltration image, recording wetting front in soil and decrease in free water level (middle of meniscus) done by Infiltrometer software
3. Calculate infiltration rate plus the degree of water retention in bed, done by Infiltrometer software F) Calculation and Reporting:
1. Data input into Infiltrometer program reports surfactant amended water infiltration rate (cm/sec in soil bed) and surfactant amended water retention as a function of distance in soil bed (% soil vol. filled with water)
2. Reconfigure data output to industry specifications and store primary data for soil type and location

Example 5

A) Soil Sample and Preparation:
1. Dry soil 40 deg. vented oven for 2 days

2. No grinding or milling
3. Sieve to −2 mm with woven sieve removes any visible plant matter etc.

B) Column Packing:
1. Column details—20 mm diam., Height 110 mm, Hydrophobic inner surface, Porous filter at bottom 11 micron hydrophilic nylon membrane
2. Weigh column with membrane
3. Packed with 3 successive soil aliquots with each tapped 3 times between additions. Final height between 7 and 8 cm. (determined automatically by image system)
4. Weigh (to determine weight of soil per column)
5. As minimum, 3 soil columns packed sequentially with consistent packing procedure C) Surfactant Preparation and Application to Soil:
1. Prepare solutions of surfactants to be tested. Concentration 4 g/L to be applied at 150 μL per soil sample
1. Soil samples (control—soil only, duplicate surfactant amended soil) 3 tubes
2. Application of surfactant by fine spray over soil surface only to duplicate tubes
3. Application of same volume of water to control
4. Dried as above 40° C. for fixed time Preparation of Sample Tubes in Optical Infiltrometer:
1. Mount filled sample tubes in tube-rack (control—soil only, duplicate surfactant amended soil)
2. Operate Infiltrometer as per operating manual Wetting Characteristic of Soil and Surfactant Modified Soil Samples:
1. Add water to control and surfactant amended columns to 20 mm above top of soil bed (constant volume liquid dispenser)
2. Simultaneously start recording infiltration image, recording wetting front in soil and decrease in free water level (middle of meniscus) done by Infiltrometer software
3. Calculate infiltration rate plus the degree of water retention in bed, done by Infiltrometer software D) Calculation and Reporting:
1. Data input into Infiltrometer program reports Surfactant amended water infiltration rate (cm/s in soil bed) and surfactant amended water retention as a function of distance in soil bed (% soil vol. filled with water)
2. Reconfigure data output to industry specifications and store primary data for soil type and location

The invention claimed is:

1. A method for indicating soil additives for improving soil water infiltration and/or modulating soil water repellence, the method comprising the steps of:
providing (S1) at least one soil sample;
preparation processing (S2) of the at least one soil sample;
providing (S3) at least one predefined amount of water to the at least one soil sample;
determining (S4) an absorbed amount of water of the at least one soil sample due to contact of the at least one soil sample with the at least one provided and predefined amount of water;
calculating (S5) an infiltration rate of the at least one soil sample based on the determined absorbed amount of water and degree of water saturation; and
indicating (S6) at least one soil additive to be used out of a list of multiple soil additives based on the calculated infiltration rate of the at least one soil sample.

2. The method according to claim 1, wherein the step of preparation processing (S2) comprises:
sieving the at least one soil sample; and/or
air drying the at least one soil sample.

3. The method according to claim 1, wherein at least one of the steps of the method is performed by high-throughput screening.

4. The method according to claim 3, wherein the method further comprises:
filling of at least one column of multiple columns of an array of soil samples.

5. The method according to claim 1, wherein the step of determining (S4) the absorbed amount of water of the at least one soil sample due to contact of the at least one soil sample with the at least one provided and predefined amount of water comprises:
recording of a wetting front over time by optical sample inspection; and/or
using an infiltrometer; and/or
using a permeameter.

6. The method according to anyone of the claim 1, wherein the step of calculating (S5) the infiltration rate of the at least one soil sample based on the determined absorbed amount of water comprises:
calculating a water infiltration time; and/or
calculating a water holding capacity.

7. The method according to claim 1, wherein the step of indicating (S6) at least one soil additive to be used based on the calculated infiltration rate of the at least one soil sample out of a list of multiple soil additives comprises:
indicating a type of the at least one soil additive to be used; and/or
indicating a concentration of the at least one soil additive to be used; and/or
indicating an amount of the at least one soil additive to be used.

8. The method according to claim 1, wherein the method further comprises the step of providing at least one soil condition and wherein the indicating (S6) of the at least one soil additive to be used is further based on the provided, at least one soil condition.

9. The method according to claim 1, wherein the at least one soil additive indicated in step (S6) is selected from surfactants, or from surface active substances.

10. The method according to claim 9, wherein the at least one soil additive indicated in step (S6) is a non-ionic surfactant.

11. The method according to claim 10, wherein the non-ionic surfactant is selected from the group consisting of ethylene oxide/propylene oxide block copolymers and C6-C20-alkylpolyglycosides.

12. An arrangement (100) for indicating soil additives for improving soil water infiltration and/or modulating soil water repellence, the arrangement comprising:
sample providing means (101) configured to provide at least one soil sample;
sample preparation means (102) configured to perform preparation processing of the at least one soil sample;
water providing means (103) configured to provide at least one predefined amount of water to the at least one soil sample;
water amount determining means (104) configured to determine an absorbed amount of water of the at least one soil sample due to contact of the at least one soil sample with the at least one provided and predefined amount of water;
infiltration rate calculating means (105) configured to calculate an infiltration rate of the at least one soil sample based on the determined absorbed amount of water and degree of water saturation;

indicating means (106) configured to indicate at least one soil additive to be used out of a list of multiple soil additives based on the calculated infiltration rate of the at least one soil.

13. The arrangement (100) according to claim 12, wherein the arrangement is a handheld arrangement.

14. The arrangement (100) according to claim 12, wherein the arrangement is configured to perform high-throughput screening.

15. The arrangement (100) according to claim 12, wherein the sample preparation means (102) are configured to
- sieve the at least one soil sample; and/or
- perform air drying of the at least one soil sample.

* * * * *